(12) United States Patent
Cole

(10) Patent No.: US 6,716,320 B1
(45) Date of Patent: Apr. 6, 2004

(54) EVAPORATION OF LIQUIDS

(76) Inventor: Michael Cole, Moor Farm, Friston, Saxmundham, IP17 1NH (GB)

(*) Notice: Subject to any disclaimer, the term of this patent is extended or adjusted under 35 U.S.C. 154(b) by 0 days.

(21) Appl. No.: 09/550,693

(22) Filed: Apr. 17, 2000

(30) Foreign Application Priority Data

| Apr. 17, 1999 | (GB) | 9908747 |
| Jun. 19, 1999 | (GB) | 9914329 |
| Aug. 12, 1999 | (GB) | 9918914 |
| Dec. 23, 1999 | (GB) | 9930292 |

(51) Int. Cl.[7] .............................. B01D 3/32; B01D 3/42
(52) U.S. Cl. ....................... 202/175; 62/5; 159/4.01; 159/6.1; 159/44; 159/901; 159/16.1; 202/160; 202/185.1; 202/238; 202/269
(58) Field of Search ................. 202/160, 175, 202/185.1, 238, 269, 205, 183, 184; 159/901, 16.1, 4.01, 44, 6.1, DIG. 40, DIG. 16; 203/49, 2, 90, 481, 98, 91, 94; 62/5

(56) References Cited

U.S. PATENT DOCUMENTS

| 3,617,208 A | * | 11/1971 | Burger | 8/142 |
| 3,893,894 A | * | 7/1975 | Humiston | 202/235 |
| 4,254,943 A | * | 3/1981 | Bjorkman | 266/149 |
| 4,549,889 A | * | 10/1985 | Yamazaki | 62/617 |
| 5,047,124 A | * | 9/1991 | Haberland | 202/181 |
| 5,082,535 A | * | 1/1992 | Oesch et al. | 202/170 |
| 5,353,519 A | * | 10/1994 | Kanamaru et al. | 34/92 |
| 5,472,575 A | * | 12/1995 | Parkinson et al. | 202/205 |
| 5,565,070 A | * | 10/1996 | Doi et al. | 203/91 |
| 5,643,418 A | * | 7/1997 | Witschi | 202/182 |
| 6,098,425 A | * | 8/2000 | Stothers | 62/635 |
| 6,224,716 B1 | * | 5/2001 | Yoder | 202/160 |
| 6,517,686 B2 | * | 2/2003 | Borzio et al. | 202/160 |

* cited by examiner

Primary Examiner—Virginia Manoharan
(74) Attorney, Agent, or Firm—Barnes & Thornburg

(57) ABSTRACT

A liquid sample 3 held in an open container 2 and including a volatile solvent, is evaporated by continuously removing inert gas rich in vapor by means of a suction tube 5 whose open end is held close to the top surface of the liquid. Vapor in the gas is then extracted in a refrigerated condensing vessel 6, from where the purified gas is fed by a pump 7 for recirculation back into a sealed chamber 1 in which the container is mounted. In a modification, the inert gas is fed directly through a nozzle 17 into the container 2 wile the gas/vapor mixture is extracted from the chamber 1 for recirculation, after passing through a condenser 6 or the like.

11 Claims, 3 Drawing Sheets

EVAPORATION OF LIQUIDS

FIELD OF INVENTION

This invention concerns evaporation of liquids.

BACKGROUND OF THE INVENTION

Directing a stream of air or an inert gas such as nitrogen onto the surface of a volatile solvent, is a technique used for evaporating such volatile liquids, but it suffers from the disadvantage that large volumes of inert gas or air, contaminated with vapour, must be disposed of. This can be expensive if the liquid is inflammable or toxic.

In one arrangement illustrated in FIG. 1 of the accompanying drawings an inert gas, which for convenience will be generally referred to herein as nitrogen, is blown onto the surface of the solvent in one or more tubes. The tubes are usually located in a housing which is not hermetically sealed and the spent nitrogen is ducted to an area, such as a fume hood, so that the nitrogen contaminated with solvent vapour is led away in a manner which is considered safe.

As mentioned, this technique uses considerable quantities of nitrogen and generates large volumes of contaminated nitrogen which can be difficult to dispose of.

It is an object of the present invention to provide an improved method for exposing volatile liquids to an inert gas during an evaporation process, which reduces the problem identified above.

SUMMARY OF THE INVENTION

According to one aspect of the present invention there is provided a method of evaporating a liquid sample including a volatile solvent, comprising the step of continuously removing inert gas which is rich in solvent vapour from near the surface of the liquid.

This allows much easier collection of any toxic or inflammable material.

The gas may be withdrawn by a suction tube which is preferably maintained close to the surface of the liquid, as the liquid level drops due to evaporation.

Advantageously the evaporation rate may be increased by imparting an orbital motion to the container holding the liquid sample, causing the latter to spin around in the form of a vortex.

Preferably a liquid sample is contained within a chamber, and the volume of permanent gas recirculated to the chamber is progressively reduced, thereby to assist evaporation.

The invention also extends to an apparatus for performing the aforesaid method.

According to another aspect of the invention there is provided an apparatus for effecting the evaporation of a volatile solvent, wherein an inert gas, which is held in a sealed environment connected to at least one container containing the solvent, is recirculated via a condensing or absorbing device for absorbing or extracting solvent vapour entrained in the recirculating inert gas.

Preferably the container holding the liquid sample is mounted in a vortex evaporator, know per se.

Other aspects of the invention are defined in the appended claims.

BRIEF DESCRIPTION OF THE INVENTION

The invention will now be described, by way of example only with reference to the accompanying a drawings in which.

DETAILED DESCRIPTION OF THE DRAWINGS

Figure 1:
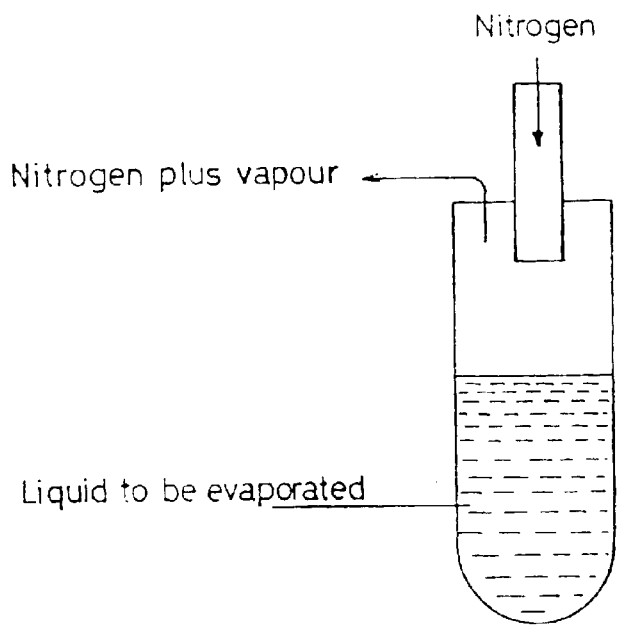
FIG. 1 is schematic view of a known device in which an inert gas, such as nitrogen, is blown down onto the surface of a liquid to be evaporated.
Figure 2:
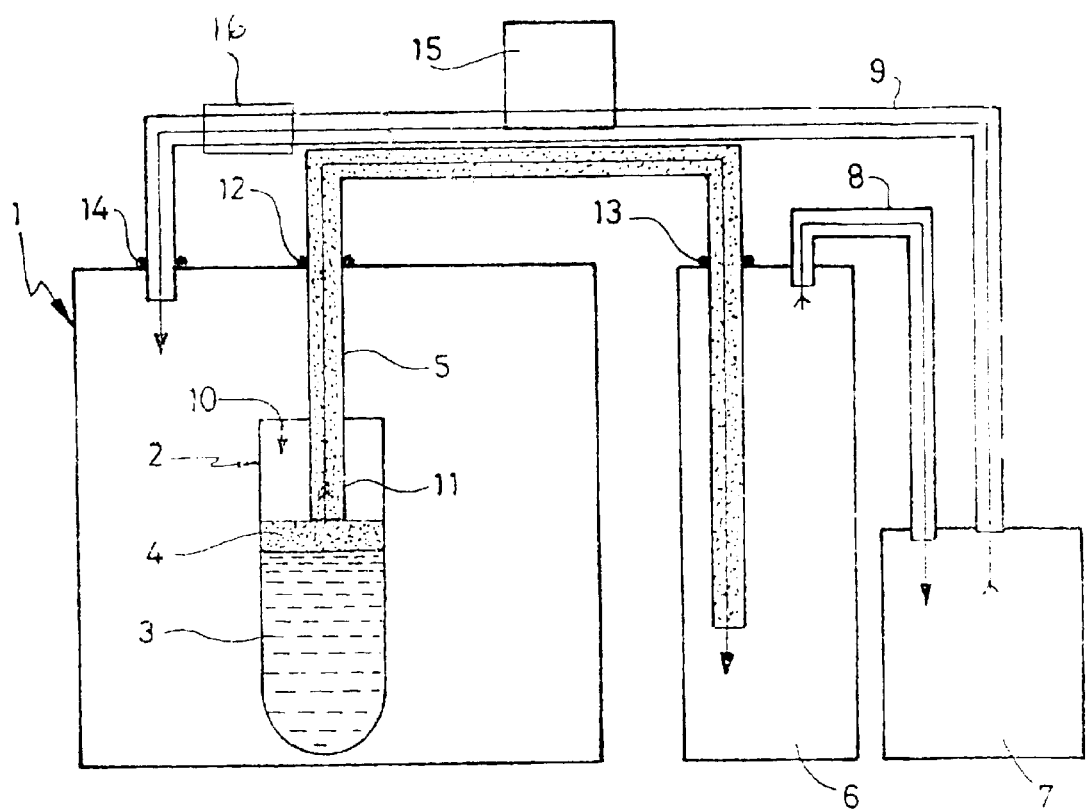
FIG. 2 shows apparatus in accordance with the invention for evaporating a volatile solvent.

In FIG. 2 a liquid sample 3 in a solvent mixture is contained in a tube container 2 inside a sealed chamber 1.

A suction tube 5 is placed with one end 11 in the container 2 at a position close above the top surface of the sample 3. This tube passes through the chamber 1 through a sealing means 12, through a further sealing means 13, and finally into a sealed refrigerated condensing vessel 6 in which the solvent vapour is stripped from the vapour/inert gas mixture.

A pipe 8 connects the refrigerated condensing vessel 6 to a pump 7 which draws the purified inert gas (eg air or nitrogen) from the vessel 6 and recirculates it through a further pipe 9 back to the chamber 1 again through a sealing means 14. From here the gas passes into the top of the container 2, as shown at 10, mixing with solvent vapour 4 which has been evaporated and passing back into the tube 5.

A heater 16, mounted around the pipe 9 near its inlet to the chamber, enables the cooled gas to be heated to a suitable temperature.

A pressure control system 15 allows the pressure in the system to be held at any required level, by venting gas to atmosphere or admitting gas into the system from a suitable source, eg a gas cylinder via a pressure regulator.

In operation the pump reduces the pressure in the refrigerated vessel 6, which causes the vapour 4 to be drawn through the tube 5 into the vessel 6 together with some inert gas, as above described. The temperature of the vessel 6 is maintained at a low enough value to condense the vapour, and any permanent gas passes through the vessel into the pump 7. Gas extracted by the pump 7 could be discharged to the atmosphere because it has been stripped of undesired vapours in the refrigerated vessel 6 or, as in this illustration, may be recirculated to continue to evaporate the sample.

If the gas from pump 7 is discharged to atmosphere, fresh gas is introduced to the chamber 1 via the pressure control means 15.

Suction by the pump 7 can, and preferable does, result in the pressure within the chamber 1 dropping as the evaporation process continues, in that the volume of air or nitrogen introduced by the control means 15 is arranged to be less than the volume of air or nitrogen withdrawn by the pump 7.

The reduced pressure in the chamber 1 assists in the evaporation of the solvent in the container 2 in a manner known per se.

The efficiency of the process is enhanced if the tube 5 is progressively lowered as the liquid level drops due to evaporation and held a few millimetres above the sample. This can be achieved manually using a means for lowering the tube 5 or raising the sample 3.

Automatic positioning can also be used, using for example optical means to sense the position of the top of the liquid sample and using a sensor system to keep the bottom of the suction tube a few millimetres above the level. Electrical proximity means could also be used to sense the level.

In the example shown, a single sample tube container is illustrated. The process can be applied equally to arrays of many tubes and blocks with numerous wells, for example microtitre plates.

Although not shown in FIG. 2, the sample tube 2 may be subjected to an orbital motion without alteration of the lateral orientation of the tube, such that the liquid 3 inside the tube moves around the tube in the form of a vortex. Such an arrangement is known per se as a vortex evaporator. The resultant agitation of the liquid in the tube increases the evaporation rate, allowing a more rapid extraction of vapour-rich gas to take place through the suction tube 5.

In place of a refrigerated condensing vessel 6, there could be substituted any suitable absorbent material, such as molecular sieves, activated charcoal, silica gel etc. In this case the gas passing back into the vessel 6 will not have been cooled, so that the heater 16 may not be required.

Figure 3:
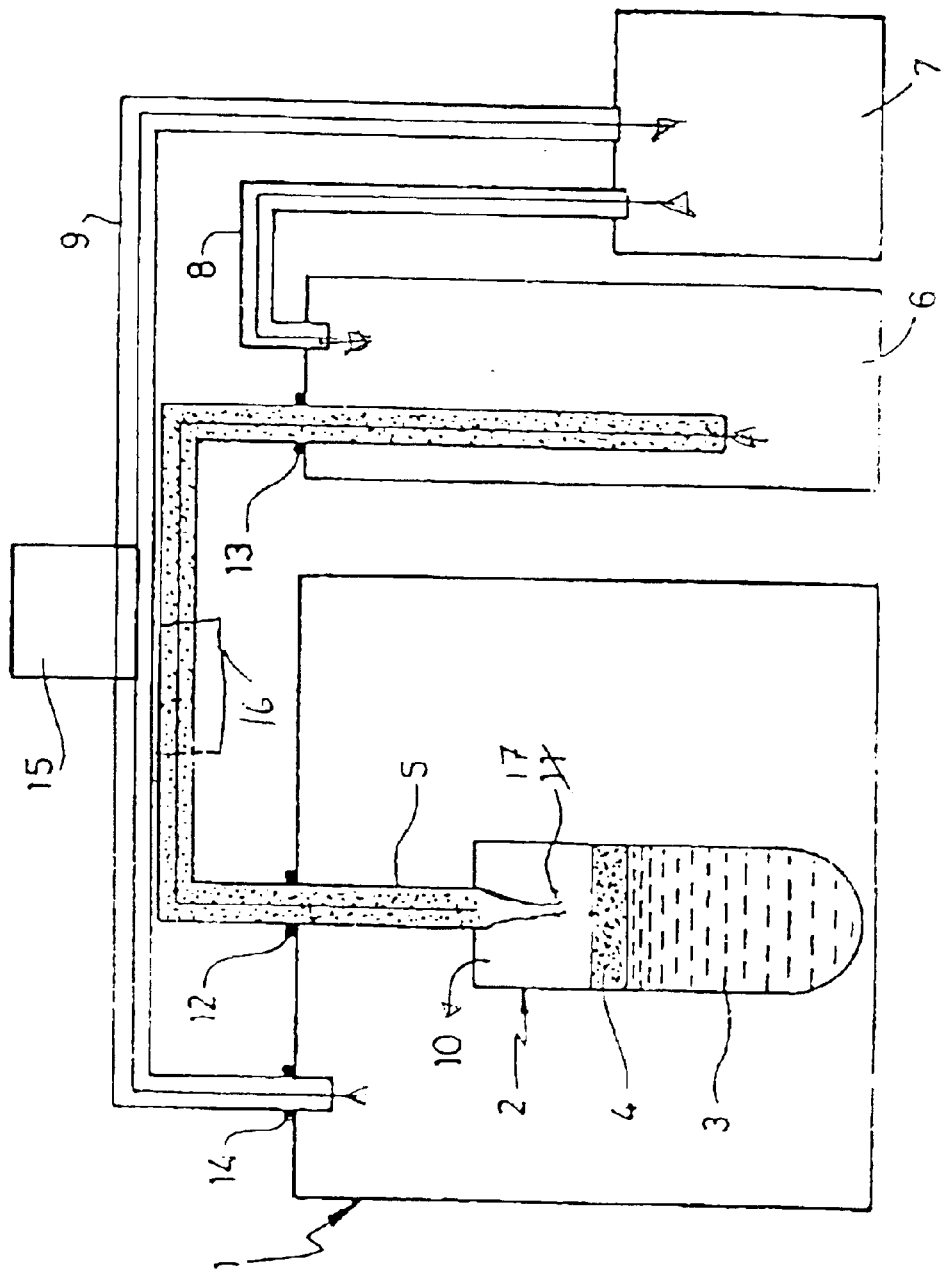
FIG. 3 shows apparatus closely similar to FIG. 2 but operating in a different manner.

Referring now to FIG. 3, there is shown a modification of the apparatus of FIG. 2 which operates in a different manner.

In this arrangement the same reference numerals are used as in FIG. 2. However, the heater 16 is here disposed around the external part of the tube 5 between the sealed chamber 1 and the condensing vessel 6. Moreover, the end of the tube 5 does not extend to a position close above the surface of the sample, but is instead shaped in the form of a nozzle 17.

In this arrangement the flow of gases and vapours in the tube 5 and pipes 8 and 9 is opposite to that shown in FIG. 2, the operation of the arrangement being as follows:

The pump 7 sucks inert gas (typically nitrogen) mixed with solvent vapour out of the scaled container 1 through the pipe 9 and passes it through the refrigerator condenser 6 or other device for absorbing or extracting the solvent vapour. The purified gas is then ducted into the tube 5 which terminates in the nozzle 17. The resultant jet of gas passing over the liquid 3 in the tube 2 tends to pick up and remove the layer of saturated vapour 4 above the liquid. The contaminated nitrogen 10 then escapes from the tube container 2 and is sucked out of the chamber 1 by the action of the pump 7, as above mentioned.

A pressure control system 15 in the pipe 9 maintains the pressure in the system at the required level by adding or removing nitrogen to or from the system. The heater 16 is used to warm the gas emerging from the condenser 6. The tube 5 and pipe 9 are sealed at 12, 13 and 14 where they enter and leave the container 1 and the condenser 6.

Although, again, only a single sample tube container 2 is illustrated, the system can be applied equally to a chamber housing a plurality of tubes, usually arranged in an array, and is equally applicable to arrangement in which the containers are replaced by blocks containing a plurality of wells, for example microtitre plates.

The or each sample tube container 2 is preferably subjected to an orbital motion without alteration of the lateral orientation of the tube, such that the liquid 3 inside the tube moves around the tube in the form of a vortex, such an arrangement being known as a vortex evaporator.

As with the apparatus of FIG. 2, the condenser 6 could be replaced by a suitable absorbent material, eg molecular sieves etc, in which case the heater 16 may again not be required.

Figure 4:
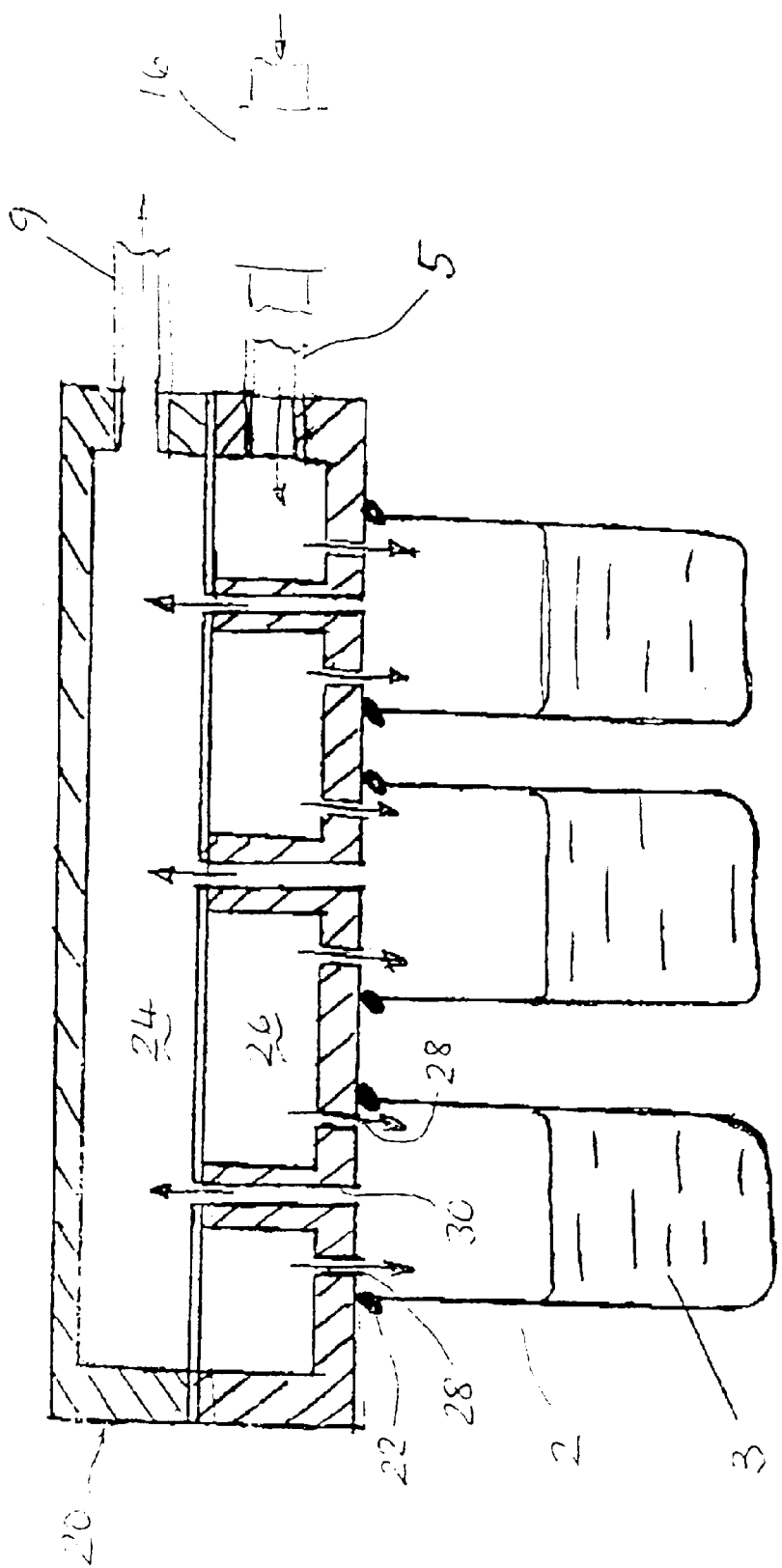
FIG. 4 shows a modification of the apparatus of FIG. 3.

Referring now to FIG. 4, there is shown a further modification of the apparatus of FIG. 3. in which the same reference numerals are used for similar parts.

Here there are three containers 2 containing liquid samples 3, only the left-hand one being referenced. The top of each container is secured to a manifold 20 by gas-tight seals 22. The manifold is divided into upper and lower compartments 24, 26, the lower of which has apertures 28 extending into the outer regions of each container 2. The upper compartment 24 is similarly provided with a passageway 30 for each container which passes through the lower compartment from the centre at the top of the container.

The lower compartment 26 is connected by the pipework 5 to the heater 16, while the upper compartment chamber 24 is connected by the pipework 9 to a pump, such as the pump 7 shown in FIGS. 2 and 3, which in turn is connected to the condenser 6.

The operation of the modified apparatus is similar to that for FIG. 3. Thus inert gas mixed with solvent vapour is drawn through the passageways 30 and the upper compartment 24 by the pump 7 and is conveyed from there to the condenser 6. At the same time purified gas, warmed by the heater 16, is ducted into the lower compartment 26, and from thence through the apertures 28 and into each container 2, so as to purge the saturated vapour above each liquid sample and enable it to be extracted through the passageways 30.

What is claimed is:

1. Apparatus for effecting the evaporation of a volatile solvent contained in a container which is mounted in a vortex evaporator, comprising a recirculating system in sealed environment means containing an inert gas and connected to said container, a condensing devise for condensing solvent vapor, and pump means for recirculating the inert gas via the condensing device, whereby solvent vapor entrained in the inert gas is condensed in the condensing device.

2. Apparatus according to claim 1 in which said container has an upper end into which the inert gas is directly returned.

3. Apparatus according to claim 2 further comprising nozzle means through which the inert gas is directed into the container directly onto the surface of the solvent in the container.

4. Apparatus according to claim 1 further comprising a pressure control means for introducing or extracting inert gas, in order to maintain a predetermined pressure in the recirculating system.

5. Apparatus according to claim 1 further comprising gas reservoir means in which inert gas is stored under pressure for reuse as required, and pressure controlling means for limiting the pressure of the gas leaving the reservoir means to a desired level.

6. Apparatus according to claim 1 in which the inert gas is nitrogen.

7. Apparatus according to claim 1 further comprising heater means provided in the recirculating system downstream of said condensing device.

8. Apparatus according to claim 1 in which said container comprises an open top for accommodation in said sealed environment means.

9. Apparatus according to claim 1 comprising a plurality of solvent containers connected to a manifold through which the inert gas is recirculated.

10. Apparatus according to claim 9 in which the manifold is divided into two compartments, one being connected to a pump for extracting the mixture of the inert gas and solvent vapor and the other feeding recirculated inert gas from the condensing device.

11. Apparatus for effecting the evaporation of a volatile solvent contained in a container, comprising scaled environment means containing an inert gas and connected to said container, a condensing device for condensing solvent vapor entrained in the inert gas is condensed in the condensing device, comprising a plurality of solvent containers connected to a manifold through which the inert gas is recirculated, in which the manifold is divided into two compartments, one being connected to a pump for extracting the mixture of the inert gas and solvent vapor and the other feeding recirculated inert gas from the condensing device.

\* \* \* \* \*

UNITED STATES PATENT AND TRADEMARK OFFICE
CERTIFICATE OF CORRECTION

PATENT NO. : 6,716,320 B1
APPLICATION NO. : 09/550693
DATED : April 6, 2004
INVENTOR(S) : Michael Cole It is certified that error appears in the above-identified patent and that said Letters Patent is hereby corrected as shown below:

In claim 11, column 4, line 61, add -- , and pump means for recirculating the inert gas via the condensing device, whereby solvent vapor -- after "a condensing device for condensing solvent vapor" and before "entrained in the inert gas is condensed in the condensing device,".

Signed and Sealed this

Eighteenth Day of March, 2008

JON W. DUDAS
*Director of the United States Patent and Trademark Office*